United States Patent [19]
Vetter et al.

[11] Patent Number: 5,833,653
[45] Date of Patent: Nov. 10, 1998

[54] PREFILLED HYPODERMIC SYRINGE

[75] Inventors: Helmut Vetter; Udo Vetter, both of Ravensburg; Thomas Otto, Weingarten; Georg Rössling, Berlin, all of Germany

[73] Assignee: Arzneimittel GmbH Apotheker Vetter & Co. Ravensburg, Ravensburg, Germany

[21] Appl. No.: 926,348

[22] Filed: Sep. 9, 1997

[30] Foreign Application Priority Data

Sep. 23, 1996 [DE] Germany .................. 196 38 940.2

[51] Int. Cl.⁶ .................................................. A61M 5/00
[52] U.S. Cl. ............................................ 604/82; 604/205
[58] Field of Search .................... 604/200, 201, 604/204, 205, 190, 224, 218

[56] References Cited

U.S. PATENT DOCUMENTS

| | | |
|---|---|---|
| 2,677,374 | 5/1954 | Burnside . |
| 3,424,155 | 1/1969 | Sarnoff . |
| 3,739,779 | 6/1973 | Pfleger ................................ 604/205 |
| 4,051,850 | 10/1977 | Tischlinger . |
| 4,051,851 | 10/1977 | Tischlinger . |
| 4,178,928 | 12/1979 | Tischlinger ..................... 604/205 X |
| 4,312,343 | 1/1982 | LeVeen et al. ................... 604/224 X |
| 4,568,336 | 2/1986 | Cooper . |
| 4,596,561 | 6/1986 | Meyer et al. ........................ 604/190 |
| 4,713,061 | 12/1987 | Tarello et al. ..................... 604/200 |
| 5,320,603 | 6/1994 | Vetter . |
| 5,354,286 | 10/1994 | Mesa . |

FOREIGN PATENT DOCUMENTS

| | | |
|---|---|---|
| 0 440 846 B1 | 6/1993 | European Pat. Off. . |
| 0 412 283 B1 | 12/1993 | European Pat. Off. . |
| 0 685 237 A3 | 12/1995 | European Pat. Off. . |
| 2 259 624 | 2/1975 | France . |
| AS 1 566 655 | 10/1967 | Germany . |
| 41 27 650 C1 | 2/1993 | Germany . |
| PS 440 561 | 12/1967 | Switzerland . |
| PS 557 684 | 1/1975 | Switzerland . |
| 1108900 | 1/1966 | United Kingdom . |

*Primary Examiner*—John D. Yasko
*Attorney, Agent, or Firm*—Herbert Dubno; Andrew Wilford

[57] ABSTRACT

A hypodermic syringe has a tubular body extending along and centered on an axis and having an axially forwardly open front end, a piston rod axially displaceable in the body and having a plunger rod extending rearwardly from the body, and a plug fitted into the front end and forming an axially through-going passage. An elastomeric membrane is provided in the plug traversing and blocking the passage. Furthermore structure fixed to the plug includes a point in the passage spaced axially slightly forward of the membrane so that the membrane can be deformed axially forward to engage and be pierced by the point.

12 Claims, 2 Drawing Sheets

PREFILLED HYPODERMIC SYRINGE

FIELD OF THE INVENTION

The present invention relates to a hypodermic syringe. More particularly this invention concerns such a syringe that is prefilled.

BACKGROUND OF THE INVENTION

As described in commonly owned U.S. Pat. No. 5,320,603, a standard hypodermic syringe has a tubular body extending along and centered on an axis and having at an axial front end a small-diameter collar formed with a front radially outwardly open seat and, axially spaced backward therefrom, a rear radially outwardly open seat. An end piece provided with a deformable plug fittable sealingly in the collar is adapted to receive a needle. Mounting formations extending axially back from the end piece engage in a front position of the end piece in the front seat and in a rear position of the end piece in the rear seat. The formations are of such an axial length that the plug is fitted snugly into the collar in the rear position but is not snugly fitted in the collar in the front position.

Thus with this system it is possible to mount the end piece in place in the front position during processing, typically lyophilization, of the medicament, and then simply push it back to the rear position to hermetically seal the syringe. This is relatively easily done under sterile circumstances, making the system ideal for use for distributing prepackaged syringe doses.

The seats are radially outwardly open grooves and the formations include a radially inwardly projecting but elastically outwardly deflectable ridge formed on a rear end of the end piece. In fact the formations are axially rearwardly extending fingers having rear ends forming the ridge and separated by notches that are radially throughgoing and axially rearwardly open. These notches afford plenty of flow cross section for devolving gases to escape from the body during lyophilization. Furthermore the end piece has a rearwardly projecting collar forming a rearwardly tapering frustoconical seat and the plug has a front end fitting complementarily in the tapering seat of the end piece. This facilitates fitting the synthetic-rubber plug in the rigid end piece. The plug itself has a rear end formed with a radially outwardly projecting annular bulge, a frustoconical intermediate surface extending from immediately forward of the bulge, and a cylindrical middle portion immediately forward of the frustoconical surface and of a diameter slightly greater than an inside diameter of the collar. This plug can hermetically seal the front end of the body.

The end piece is formed with a forwardly projecting and axially centered tubular extension and the plug has a forward extension fitting complementarily in the end-piece extension. A tip cap is normally fitted over the end-piece extension and blocks a front end of the passage.

The hypodermic syringe further has according to this earlier invention a protector ring displaceable on the end piece between a front position mounted thereon forward of the formations and a rear position engaged around the formations and holding same in the rear position of the end piece in the rear seat against deflection therefrom. Thus when it is pushed back the protector ring prevents subsequent accidental or intentional removal of the end piece and its plug. The end cap and the protector ring are formed with a ridge and groove that radially interfit in the front position of the ring. In addition the protector ring is provided with a protector cap and is connected to it via a weakened-line region permitting the cap to be snapped off the ring. The end piece is formed with a forwardly projecting and axially centered tubular extension and the plug has a forward extension fitting complementarily in the end-piece extension. In this case the protector cap is formed with a central observation hole aligned with the tip cap but of too small a size for the tip cap to fit through. The protector cap has a front wall sitting on a front face of the tip cap in the rear position of the protector ring.

The body is formed with an axially extending and radially outwardly projecting ridge. The syringe further has according to the invention a plunger fitting over the body and having an axially extending and inwardly open groove fitting over the ridge.

Such a syringe is therefore sealed by the plug and tip cap so that there is not only the joint between the end plug and the collar, but another joint where the tip cap fits into the passage of the plug. Not only does this construction present two sites for possible leakage and contamination, but it also means that the medicament in the syringe is in contact with the materials of the tip cap and end piece.

OBJECTS OF THE INVENTION

It is therefore an object of the present invention to provide an improved prefilled syringe.

Another object is the provision of such an improved prefilled syringe which overcomes the above-given disadvantages, that is which is particularly well sealed and where the contained medicament contacts a minimum of different materials prior to fitting of the needle or cannula and expression from the syringe.

SUMMARY OF THE INVENTION

A hypodermic syringe has according to the invention a tubular body extending along and centered on an axis and having an axially forwardly open front end, a piston rod axially displaceable in the body and having a plunger rod extending rearwardly from the body, and a plug fitted into the front end and forming an axially throughgoing passage. According to the invention an elastomeric membrane is provided in the plug traversing and blocking the passage. Furthermore structure fixed to the plug includes a point in the passage spaced axially slightly forward of the membrane so that the membrane can be deformed axially forward to engage and be pierced by the point.

Thus with this system if the contents of the syringe is pressurized to bow the membrane forward, it will come into contact with the point to pierce this membrane and allow the contents to be expressed. Nonetheless prior to such action the contents will be hermetically contained, contacting nothing but the syringe body, piston, plug, and membrane. The chance of leakage or contamination is therefore greatly reduced.

In accordance with the invention the body has a rear end provided with an internal screwthread and the plunger rod is formed with a complementary external screwthread. This allows the piston to be advanced with great force but very slowly to pierce the membrane. The screwthreads are fairly short so that they only serve for initial pressurization of the syringe and piercing of the membrane. After a short axial travel via the screwthreads, the screwthreads disengage and the plunger can be advanced normally.

Furthermore according to the invention the plug is relatively soft and includes a hard ring set in the passage immediately downstream of the membrane and formed with the point. The passage and ring have a complementary double frustoconical shape, with a pair of opposite flared frustoconical sections centered on the axis and tapered away from each other. The ring has a rear end resting against the membrane.

A filter screen is set in the passage downstream of the membrane. This screen is therefore a cheap but permanent part of the disposable syringe assembly and ensures that any particles, for instance bits of the membrane dislodged by the point, in the syringe will not get to the cannula eventually fitted to the end piece. Since the screen is part of the assembly it is impossible for the nurse or doctor to forget to install it. Furthermore it remains sterile in the syringe prior to use, but is out of contact with the medicament.

The end piece according to the invention is a sleeve having a rear end engaged around the front end of the body. This front end is formed with a front radially outwardly open groove and, spaced axially backward therefrom, a rear radially outwardly open groove. The sleeve rear end is formed with a radially deflectable inwardly projecting ridge engageable in the grooves and is formed with at least one axially backwardly extending and open slot. The plug sits in the end piece so that if the contents are to be sterilized or lyophilized, the end piece and plug are positioned in a front position engaged in the front groove with the slot forming a vent for the interior of the syringe. Once the operation is complete the end piece is pushed into a rear position in which it fits in the rear groove and the plug hermetically closes the body front end.

The hypodermic syringe in accordance with the invention further has a protector sleeve engaged around the end piece and retaining same on the body and a tip cap engaged over a front end of the end piece. The protector sleeve covers and holds the tip cap in place. This protector sleeve has a rear part engaged around the front end of the body, a front part formed as a cap engaging over the tip cap, and a frangible web interconnecting the parts. The front end can be broken off to allow the tip cap to be removed for fitting a needle or cannula to the end piece.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
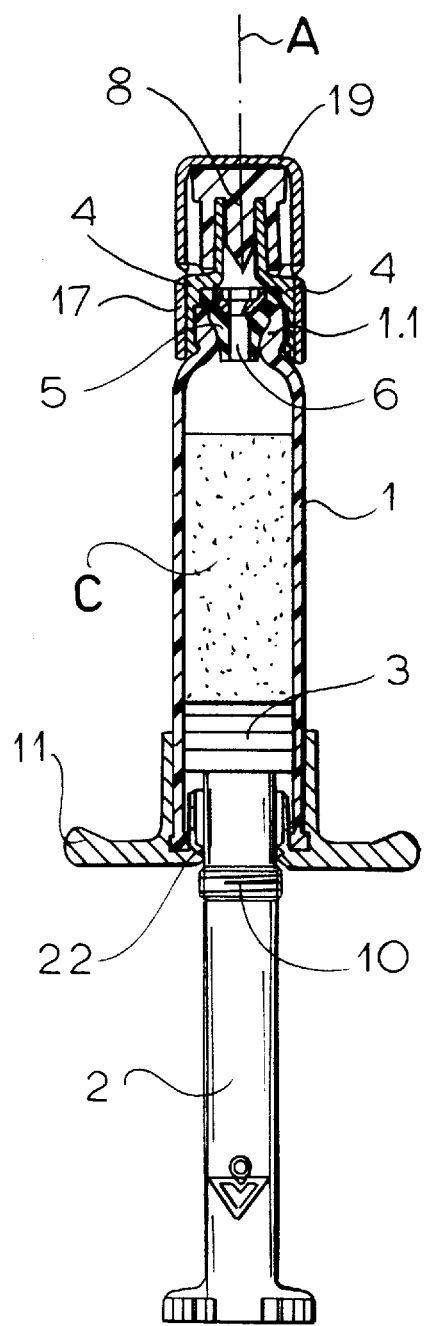
FIG. 1 is an axial section through the syringe according to the invention.
Figures 2, 3:
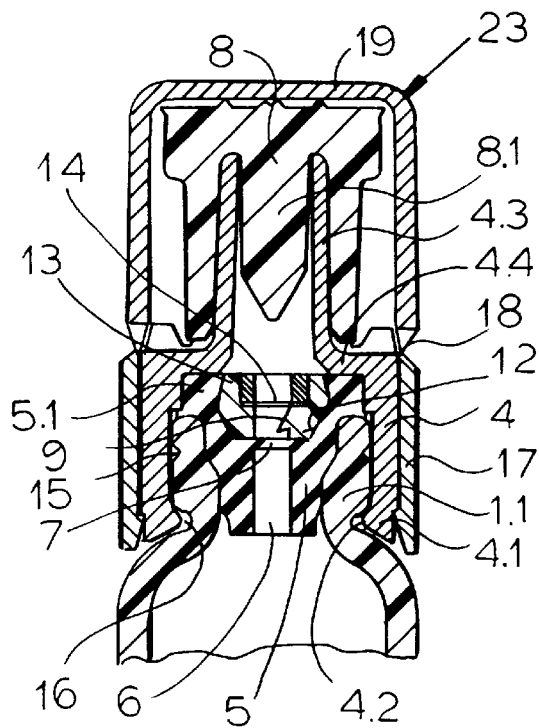
FIG. 2 is a large-scale view of the upper end of the syringe of FIG. 1.
FIG. 3 is a larger-scale view of the plug of the syringe.

As seen in FIGS. 1 and 2 a syringe according to this invention has a basically cylindrical transparent glass or plastic body 1 centered on an axis A and having a front end formed by a small-diameter tubular collar 1.1 in turn formed with a radially outwardly open front groove 15 and a radially outwardly open rear groove 16. An end piece 4 is provided with a holding skirt 4.1 formed with a radially inwardly projecting ridge 4.2 engaged prior to processing of contents C of the body 1 in the front groove 15 and thereafter in the rear groove 16 as described in the above-identified commonly owned patent. The body 1 is provided with a finger crosspiece 11 and with an axially displaceable piston 3 carried on a plunger or piston rod 2.

The end piece 4 as better shown in FIG. 2 has a transverse stepped part 4.4 fitted complementarily over a forwardly frustoconically flared front-end flange 5.1 of an elastomeric plug 5. The holding skirt 4.2 is actually formed by an angularly equispaced array of axially rearwardly projecting fingers separated by axially rearwardly and radially throughgoing spaces or notches. The inner faces of the rear ends of the fingers are formed with bosses that constitute the ridge 4.1 that sits in either of the seat grooves 16 and 15.

According to the invention the plug 5 is formed with an axially centered and rearwardly open blind passage 6 and, closing the front end of this passage 6, with an integral elastomeric membrane 7. In addition the plug 5 is formed centered on the axis A with a double frustoconical seat 12 in which is received a hard plastic ring element 13 formed with a point 9 juxtaposed with but spaced forwardly of the membrane 7. Another ring 20 set in the ring 13 holds a filter screen 14 across a passage 21 formed by the element 13 in line with the passage 6.

The piston rod or plunger 2 is formed with an external screwthread 10 and the finger crosspiece 11 with a complementary internal screwthread 22. This allows the piston 3 to be advanced slowly but with great force so as to pressurize the interior of the body 1. When pressurized the membrane 7 will bow upward as shown in dashed lines in FIG. 3 to engage the point 9 which will pierce it neatly.

A small-diameter forward extension 4.3 forming the front end of the end piece 4 receives a rearwardly extending pin 8.1 of a standard plastic tip cap 8. In turn a protector sleeve 23 centered on the axis A has a rear end 17 engaged snugly around the rear end 4.1 of the end piece 4, a front end 19 formed as a cap fitted over the tip cap 8, and a thin frangible web 18 joining the two parts 17 and 19. The forward extension 4.3 serves for mounting an actual cannula or needle on the syringe according to the invention.

We claim:

1. A hypodermic syringe comprising:

a tubular body extending along and centered on an axis and having an axially forwardly open front end;

a piston rod axially displaceable in the body and having a plunger rod extending rearwardly from the body;

a relatively soft plug fitted into the front end and forming an axially throughgoing passage;

a hard ring set in the passage;

an elastomeric membrane in the plug immediately upstream of the ring traversing and blocking the passage; and structure fixed to the plug including a point formed on the ring and spaced axially slightly forward of the membrane, whereby the membrane can be deformed axially forward to engage and be pierced by the point.

2. The hypodermic syringe defined in claim 1 wherein the body has a rear end provided with an internal screwthread and the plunger rod is formed with a complementary external screw-thread.

3. The hypodermic syringe defined in claim 1 wherein the passage and ring have a complementary double frustoconical shape.

4. The hypodermic syringe defined in claim 3 wherein the double frustoconical shape has a pair of opposite flared frustoconical sections centered on the axis and tapered away from each other.

5. The hypodermic syringe defined in claim 1 wherein the ring has a rear end resting against the membrane.

6. The hypodermic syringe defined in claim 1, further comprising a filter screen set in the passage downstream of the membrane.

7. The hypodermic syringe defined in claim 1 wherein the end piece is a sleeve having a rear end engaged around the front end of the body.

8. The hypodermic syringe defined in claim 7 wherein the front end is formed with a front radially outwardly open groove and, spaced axially backward therefrom, a rear radially outwardly open groove, the sleeve rear end being formed with a radially deflectable inwardly projecting ridge engageable in the grooves.

9. The hypodermic syringe defined in claim 8 wherein the sleeve rear end is formed with at least one axially backwardly extending and open slot.

10. The hypodermic syringe defined in claim 1, further comprising a protector sleeve engaged around the end piece and retaining same on the body.

11. The hypodermic syringe defined in claim 10, further comprising a tip cap engaged over a front end of the end piece, the protector sleeve covering and holding the tip cap in place.

12. The hypodermic syringe defined in claim 11 wherein the protector sleeve has a rear part engaged around the front end of the body, a front part formed as a cap engaging over the tip cap, and a frangible web interconnecting the parts.

\* \* \* \* \*